United States Patent [19]
Hess

[11] Patent Number: 5,542,912
[45] Date of Patent: Aug. 6, 1996

[54] FOOT SPLINT

[75] Inventor: Clarence E. Hess, Safety Harbor, Fla.

[73] Assignee: Restorative Care of America Incorporated, Clearwater, Fla.

[21] Appl. No.: 370,188

[22] Filed: Jan. 9, 1995

[51] Int. Cl.$^6$ ................................................. A61F 5/00
[52] U.S. Cl. ......................... 602/27; 602/28; 602/16; 128/882
[58] Field of Search ................................. 602/5, 16, 23, 602/27–29, 18; 128/882

[56] References Cited

U.S. PATENT DOCUMENTS

| | | |
|---|---|---|
| 830,894 | 9/1906 | Garrod . |
| 1,638,285 | 8/1927 | Brooks . |
| 3,976,059 | 8/1976 | Lonardo . |
| 4,735,196 | 4/1998 | Krag et al. ............................ 602/18 |
| 4,913,135 | 4/1990 | Mattingly ............................ 602/18 |
| 4,919,118 | 4/1990 | Morris ............................ 602/27 X |
| 5,014,690 | 5/1991 | Hepburn et al. . |
| 5,195,947 | 3/1993 | Bode ............................ 602/18 |
| 5,224,925 | 7/1993 | Varn . |

FOREIGN PATENT DOCUMENTS

| | | | |
|---|---|---|---|
| 523538 | 8/1921 | France | ............................ 602/28 |

Primary Examiner—Linda C. Dvorak
Attorney, Agent, or Firm—Zarley, Mckee, Thomte, Voorhees & Sease

[57] ABSTRACT

A plastic foot splint is provided which has a back portion, a heel portion, and a foot portion. A diagonally extending frame connects the heel and the foot portions. The frame is substantially rectangular in shape and has parallel spaced upper and lower brackets with the upper bracket being connected to the leg portion of the splint and the lower bracket being connected to the bottom of the foot portion of the splint. The opposite ends of the brackets are connected by pairs of arms with each pair of arms being comprised of a first arm element threadably extending into a second arm element so that the threadable engagement therebetween determines the effective length of each pair of arms. The first arm element is an elongated threaded cylinder-shaped screw with an elongated planar portion thereon, with indicia marks on the planar portion to permit visual detection of the threadable extension of the first arm element into the second arm element. The upper end of each pair of arms is pivotally secured respectively to one of the opposite ends of the upper bracket, and the lower end of each pair of arms is rotatably secured respectively to one of the opposite ends of the lower bracket. The threadable engagement of the lower arm element into the upper arm element fixes the effective length of the arm until the lower arm element is again manually rotated to increase or decrease the effective length of the arm.

14 Claims, 1 Drawing Sheet

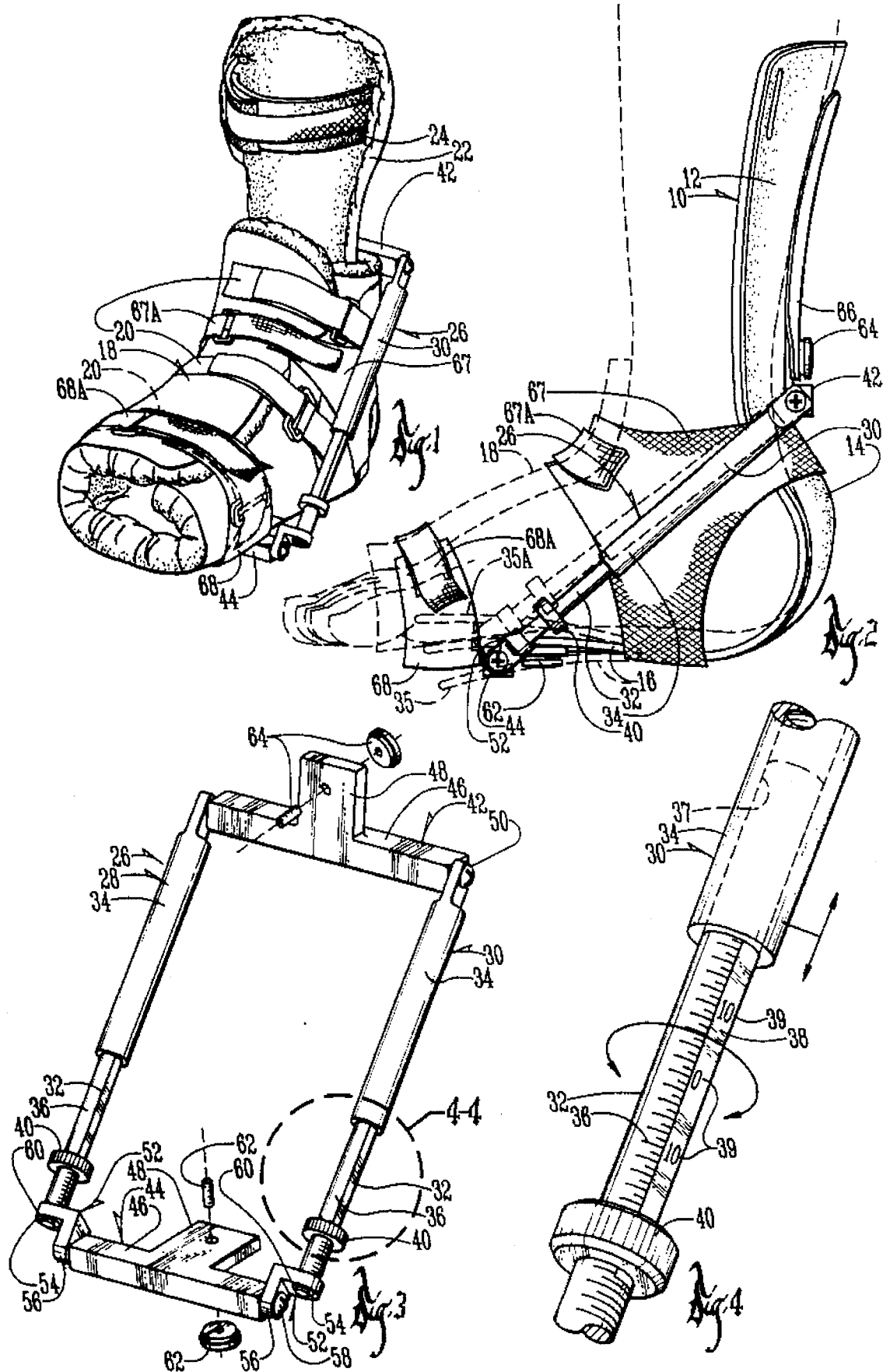

FOOT SPLINT

BACKGROUND OF THE INVENTION

This invention is an improvement over that of U.S. Pat. No. 5,224,925 issued Jul. 6, 1993.

Bedfast patients often experience a drop-foot condition wherein the foot is extended and forms an obtuse angle with respect to the leg. If the condition is not rectified, the foot may become rigidly affixed in the extended position which will prevent the patient from walking when out of bed.

Patients suffering from spinal injuries often suffer from the drop-foot condition, and the feet are commonly subjected to spasms as well.

The splint of U.S. Pat. No. 3,976,059 is adapted to deal with the drop-foot condition wherein the inherent spring like characteristics of the splint material tend to draw the extended foot back towards its normal position. However, the use of such a splint to correct the drop-foot situation is extremely slow and there is no way to program the splint to deal with predetermined increments of foot extension.

Commonly, the extended foot is partially subjected to dorsiflexion wherein the foot is partially moved back towards its normal position. The foot is then encased in a rigid cast and left for a period of time whereupon the cast is then removed, additional dorsiflexion is applied, and a new cast is placed on the foot. This process is repeated with a plurality of subsequent casts whereupon the foot is returned to its normal angular position with respect to the leg.

It is therefore an object of this invention to provide a foot splint which can effectively deal with incremental corrections of drop-foot extension without the use of plaster casts.

A further object of this invention is to provide a foot splint which can be adjusted to incremental angular positions and locked in such positions to deal with any angular displacement of the foot being experienced by a given patient.

A still further object of this invention is to provide a foot splint which can be easily moved to and maintained in a given position in the process of dealing with drop-foot conditions existing in bedfast patients.

These and other objectives will be apparent to those skilled in the art.

SUMMARY OF THE INVENTION

A plastic foot splint is provided which has a back portion, a heel portion, and a foot portion. The foot portion is joined to the back portion by the heel portion and is normally positioned at a substantial right angle with respect to the leg portion.

The splint is comprised of a resilient springlike material to permit the foot portion to be forcibly deflected at the heel portion to create an obtuse angle with respect to the leg portion. The foregoing structure exists in the prior art.

The device of this invention includes a diagonally extending frame which connects the heel and the foot portions. The frame is substantially rectangular in shape and has parallel spaced upper and lower brackets with the upper bracket being connected to the leg portion of the splint and the lower bracket being connected to the bottom of the foot portion of the splint. The opposite ends of the brackets are connected by pairs of arms with each pair of arms being comprised of a first arm element threadably extending into a second arm element so that the threadable engagement therebetween determines the effective length of each pair of arms.

The first arm element is an elongated threaded cylinder-shaped screw with an elongated planar portion thereon, with indicia marks on the planar portion to permit visual detection of the threadable extension of the first arm element into the second arm element. The upper ends of each pair of arms is pivotally secured to the opposite ends of the upper bracket, and the lower ends of each pair of arms is rotatably secured to the opposite ends of the lower bracket. The threadable engagement of the lower arm element into the upper arm element fixes the effective length of the arm until the lower arm element is again manually rotated to increase or decrease the effective length of the arm.

BRIEF DESCRIPTION OF THE DRAWINGS

FIG. 1 is a perspective view of the splint or orthosis of this invention;

FIG. 2 is an enlarged scale side elevational view of the device of FIG. 1 showing the outline of a patient's foot in dotted lines;

FIG. 3 is an enlarged scale perspective view of the frame of this invention; and FIG. 4 is an enlarged perspective view of the portion of FIG. 3 as viewed on line 4—4 of FIG. 3.

DESCRIPTION OF THE PREFERRED EMBODIMENT

The plastic splint 10 has all of the characteristics of the plastic splint disclosed in U.S. Pat. No. 3,976,059. The splint 10 includes a back portion 12, a heel portion 14, and a foot portion 16. As described in the aforesaid patent, the heel portion 14 has a curvature greater than the normal curvature of a patient's heel to provide space between the heel of the patient and the heel portion 14.

A padded sandal 18 with attachment straps 20 serves to connect the splint 10 to the foot of a patient. A conventional leg pad 22 with attachment straps 24 further serves to stabilize the back portion 12 of the splint to the leg of the patient. All of the aforementioned structure is conventional.

The frame 26 shown in FIG. 3 is an improvement over the aforesaid U.S. Pat. No. 5,224,925 in that it is more easily operated and controlled, and provides a more precise way of adjustment when the foot portion 16 is angularly moved with respect to back portion 12.

Frame 26 has a pair of arms 28 and a pair of arms 30. Each pair of arms is comprised of a first arm element 32 which is threadably inserted at its upper end into the lower end of second arm element 34. The first arm element 32 is a cylindrical elongated bolt with threads 36 on the outer surface thereof which are compatible with internal threads (not shown) in the center bore of 37 of second arm element 34 (FIG. 4). An elongated planar surface 38 is machined on one side of the first arm element 32 and a plurality of spaced indicia marks or numerals 39 are imposed on surface 34. The indicia numerals 39 provide a visual means for the operator to visually determine the amount of penetration that arm element 32 has with respect to the arm element 34. A cylindrical rotator knob 40 is rigidly mounted by a set screw or the like (not shown) to the lower end of first arm element 32 to facilitate the rotation of arm element 32 into arm element 34.

Frame 26 also includes an upper bracket 42 and a lower bracket 44, each of which is comprised of a lateral extending bar portion 46 and a protruding tab 48 (FIG. 4). The upper bracket 42 is pivotally secured to the upper ends of arm elements 34 by pins or screws 50. L-shaped connectors 52 comprising perpendicularly disposed legs 54 and 56 connect the opposite ends of lower bracket 42 to the lower ends of first arm elements 32. Pins or screws 58 extending through legs 56 into the ends of bracket 44 effect the pivotal connection between the connectors 52 and the bracket 54. The lower ends of arm elements 32 are rotatably, but not threadably, mounted within a suitable aperture in the legs 54 of connectors 52. Snap washers or the like 60 (FIG. 3) secure the lower ends of arms 32 within the apertures of legs 54.

Nut and bolt assemblies 62 and 64 (FIG. 3) extending through suitable apertures in tabs 48 of brackets 42 and 44 serve to connect the brackets 42 and 44 to the back portion 12 and the foot portion 16, respectively. A conventional stabilizer bar 66 (FIG. 2) on the back of splint 10 is pivotally mounted to the splint by the nut and bolt assembly 64.

A heel strap 67 with fastener 67A (FIG. 2) fits over the heel portion and upper sandal 18, and a toe strap 68 with fastener 68A fits over the toe area of sandal 18.

The foregoing structure permits the angle between the back portion 12 and the foot portion 16 to be increased or decreased by 1½ degrees per revolution of the arm element 32 with respect to the arm element 34. The dotted lines at numerals 35 and 35A show alternate positions of the foot portion when moved to an increased or decreased angular position with respect to the back portion. Preferably, the foot and the back portion can thereupon have their angular positions varied from a normal position of approximately 90 degrees to 30 degrees plantar flexion to 10 degrees dorsiflexion to meet individual patient needs. The degree of angular displacement can be visually discerned by the indicia numerals 39 on planar surface 38. The numerals 39 designate degrees.

As indicated above, the effective length of pairs of arms 28 and 30 is effected by manually turning rotator knobs 40 in a direction to increase or decrease the length of the arms. Rotating the knobs 40 in a clockwise direction as viewed from the bottom of FIG. 4 will decrease the angle, and a counter clockwise motion will increase the angle. Again, each revolution of the rotator knob and arm element 32 will increase or decrease the angle by 1 ½ degrees.

No separate stop element or locking element is required by the foregoing structure because the threaded relationship between arm elements 32 and 34 serves to maintain the angular displacement between the back portion 12 and the foot portion 16 without any further locking action.

From the foregoing, it is seen that this invention will achieve at least its stated objectives.

What is claimed is:

1. A foot splint, comprising, a splint having a back portion, a heel portion and a foot portion, said foot portion being joined to said back portion by said heel portion, and normally being positioned at a substantial right angle with respect to said leg portion, said splint being of resilient material to permit said foot portion to be forcibly deflected at said heel portion to create an obtuse angle with respect to said leg portion, said back portion being adapted to engage the rearward portion of the calf of a patient's leg, a frame secured to said back portion above said heel portion and extending forwardly and downwardly to a point of connection with said foot portion, so as to form downwardly extending diagonal arms between said back portion and said foot portion;

said arms comprising first and second pairs of arms, said pairs of arms comprising a first arm element threadably extending into a second arm element so that the threadable engagement of said first and second arm elements determine the effective length of each pair of arms;

said first arm element being an elongated threaded cylindrical-shaped screw with an elongated planar portion thereon, and indicia means on said planar portion to permit visual detection of the threadable extension of said first arm element into said second arm element.

2. The device of claim 1 wherein said first arm element has a rotation element fixed thereto to permit manual rotation of said first arm element.

3. A foot splint, comprising, a splint having a back portion, a heel portion and a foot portion, said foot portion being joined to said back portion by said heel portion, and normally being positioned at a substantial right angle with respect to said leg portion, said splint being of resilient material to permit said foot portion to be forcibly deflected at said heel portion to create an obtuse angle with respect to said leg portion, said back portion being adapted to engage the rearward portion of the calf of a patient's leg, a frame secured to said back portion above said heel portion and extending forwardly and downwardly to a point of connection with said foot portion, so as to form downwardly extending diagonal arms between said back portion and said foot portion;

said arms comprising first and second pairs of arms, said pairs of arms comprising a first arm element threadably extending into a second arm element so that the threadable engagement of said first and second arm elements determine the effective length of each pair of arms;

said frame comprising an upper bracket pivotally secured to an upper end of said second arm elements, and a lower bracket rotatably and pivotally secured to a lower end of said first arm elements; and an L-shaped connector connecting opposite ends of said lower bracket to the lower ends of said first arm elements.

4. The device of claim 3 wherein said L-shaped connectors have first legs pivotally connected to opposite ends of said lower bracket, and second legs rotatably connected to the lower ends of said first arm elements.

5. A foot splint, comprising, a splint having a back portion, a heel portion and a foot portion, said foot portion being joined to said back portion by said heel portion, and normally being positioned at a substantial right angle with respect to said leg portion, said splint being of resilient material to permit said foot portion to be forcibly deflected at said heel portion to create an obtuse angle with respect to said leg portion, said back portion being adapted to engage the rearward portion of the calf of a patient's leg, a frame secured to said back portion above said heel portion and extending forwardly and downwardly to a point of connection with said foot portion, so as to form downwardly extending diagonal arms between said back portion and said foot portion;

said arms comprising first and second pairs of arms, said pairs of arms comprising a first arm element threadably extending into a second arm element so that the threadable engagement of said first and second arm elements determine the effective length of each pair of arms;

said first arm element having a rotation element fixed thereto to permit manual rotation of said first arm element in either direction.

6. The device of claim 5 wherein said rotation element is a cylindrical knob surrounding said first arm.

7. The device of claim 5 wherein said first arm element has a lower end rotatably secured to said frame.

8. The device of claim 5 wherein said second arm element has an upper end pivotally secured to said frame.

9. The device of claim 5 wherein said first arm element has a lower end rotatably secured to said frame, and wherein said second arm element has an upper end pivotally secured to said frame.

10. The device of claim 5 wherein said frame comprises an upper bracket pivotally secured to an upper end of said second arm elements, and a lower bracket rotatably and pivotally secured to a lower end of said first arm elements.

11. The device of claim 10 wherein said upper and lower brackets each have a center tab for effecting connection thereof to said back portion and said heel portion, respectively.

12. The device of claim 11 wherein said tabs are secured to said splint by first and second nut and bolt assemblies, respectively.

13. The device of claim 12 wherein a stabilizer bar is secured to said splint by said first nut and bolt assemblies.

14. The device of claim 10 wherein said upper and lower brackets are of the same size and shape.

\* \* \* \* \*